(12) United States Patent
Sasaki et al.

(10) Patent No.: US 8,283,337 B2
(45) Date of Patent: Oct. 9, 2012

(54) THERAPEUTIC OR PROPHYLACTIC AGENT FOR VASOCONSTRICTION

(75) Inventors: Nobuo Sasaki, Tokyo (JP); Yuichi Tei, Tokyo (JP); Ryosuke Echigo, Tokyo (JP); Shigeki Suzuki, Tokyo (JP); Touru Hakukawa, Tokyo (JP)

(73) Assignees: Next21 K.K., Tokyo (JP); The Universtiy of Tokyo, Tokyo (JP)

( * ) Notice: Subject to any disclaimer, the term of this patent is extended or adjusted under 35 U.S.C. 154(b) by 417 days.

(21) Appl. No.: 12/528,116

(22) PCT Filed: Feb. 22, 2008

(86) PCT No.: PCT/JP2008/000306
§ 371 (c)(1),
(2), (4) Date: Sep. 4, 2009

(87) PCT Pub. No.: WO2008/102563
PCT Pub. Date: Aug. 28, 2008

(65) Prior Publication Data
US 2010/0035837 A1 Feb. 11, 2010

(30) Foreign Application Priority Data
Feb. 23, 2007 (JP) ................................. 2007-044744

(51) Int. Cl.
*A01N 43/04* (2006.01)
*A61K 31/715* (2006.01)
*C13K 5/00* (2006.01)
*C13K 7/00* (2006.01)

(52) U.S. Cl. .................. 514/53; 536/123.13

(58) Field of Classification Search ................. None
See application file for complete search history.

(56) References Cited

U.S. PATENT DOCUMENTS

| | | | |
|---|---|---|---|
| 5,637,309 A | 6/1997 | Tajima et al. | |
| 5,726,209 A | 3/1998 | Flaim et al. | |
| 5,981,498 A | 11/1999 | Fukuda et al. | |
| 6,232,294 B1 * | 5/2001 | Fukuda et al. | 514/42 |
| 6,593,329 B1 | 7/2003 | Lehtonen et al. | |
| 7,186,824 B2 * | 3/2007 | Aga et al. | 536/123.13 |
| 7,854,922 B2 * | 12/2010 | Tanabe et al. | 424/70.13 |
| 7,994,155 B2 * | 8/2011 | Oku et al. | 514/61 |
| 2003/0059479 A1 * | 3/2003 | Miyake | 424/539 |
| 2005/0181044 A1 | 8/2005 | Romero | 424/464 |
| 2007/0140984 A1 * | 6/2007 | Kusano et al. | 424/49 |
| 2007/0167396 A1 * | 7/2007 | Dillon et al. | 514/54 |

FOREIGN PATENT DOCUMENTS

| | | |
|---|---|---|
| JP | 7-89876 A | 4/1995 |
| JP | 11-171778 A | 6/1999 |
| JP | 11-507351 A | 6/1999 |
| JP | 2000-191540 A | 7/2000 |
| JP | 2003-503353 A | 1/2003 |
| WO | 2005/037236 A2 | 4/2005 |

OTHER PUBLICATIONS

English translation of the PCT International Preliminary Report on Patentability (IPRP) issued Sep. 11, 2009, in International Patent Application No. PCT/JP2008/000306. (8 pages).
International Search Report w/translation from PCT/JP2008/000306 dated Apr. 8, 2008 (6 pages).
Written Opinion from PCT/JP2008/000306 dated Apr. 8, 2008 (4 pages).
Patent Abstracts of Japan; Publication No. 11-171778 dated Jun. 29, 1999; Hayashibara Biochem Lab Inc. (1 pages).
Chen, et al.; "Atarashii Zoki Hozon'eki (ET-Kyoto-eki) no Kaihatsu" (translated as Development of New Organ Preservation Solution (ET-Kyoto solution)); Organ Biology, vol. 12, No. 1, 2005, pp. 9 to 20 (13 pages).
Yamazaki, Kazuhiro et al.; "Kyoketsu Saikanryu Shogai ni Chakumoku shita Shinkin Hogoho to Shinkin Hogoeki no Kento"; Journal of Japan Surgical Society, 105 (special extra issue), p. 566 (abstract No. PS-147-2); 2004 (2 pages).
Nakane, Hiroshi; "Nokekkan Shogai to Sanka Stress"; Molecular Cardiovascular Medicine, vol. 3 No. 4; 2002; pp. 455 to 462 (9 pages).
Yada, Toyotaka; "Bisho Junkan ni Okeru Naihi Izonsei Ketsuryu Chosetsu Inshi no Yakuwari"; Kessen Shiketsushi; vol. 16 No. 4; 2005; pp. 425 to 428 (6 pages).
Tahara, Shunsuke et al.; "Junkanki Shikkan to Rho Kinase"; Circulation Control; vol. 27 No. 2; 2006; pp. 121 to 129 (10 pages).
Tanaka, Hidetoshi et al.; "Hikinuki Sonsho Kekkan ni Okeru Reperfusion Injury to Setchaku Inshi (ICAM-1) no Hatsugen ni Tsuite"; Dai 26 Kai Nippon Microsurgery Gakujutsu Shukai Shoroku; 2000; p. 186 (2 pages).
Levitsky, J. et al.; Sodium Ion/Hydrogen Ion Exchange Inhibition: A New Pharmacologic Approach to Myocardial Ischemia and Reperfusion Injury; J. Clin. Pharmacol.; vol. 38 No. 10; 1998; pp. 887-897 (12 pages).
espacenet.com Abstract Publication No. JP11507351 dated Jun. 29, 1999; Alliance Pharmaceutical Corp. (1 page). Patent Abstracts of Japan; Publication No. 07-089876 dated Apr. 4, 1995; Shiseido Co. Ltd. (1 page).
espacenet.com Abstract Publication No. EP1016411 dated Jul. 5, 2000 (corresponds to JP2000-191540A); Lakaro Biopharmaceutical Inc. (1 page).
Mayberg, M.R., M.D. et al.; "Guidelines for the Management of Aneurysmal Subarachnoid Hemorrhage, A Statement for Healthcare Professionals From a Special Writing Group of the Stroke Council, American Heart Association"; Circulation vol. 90 No. 5; 1994; pp. 2592-2605 (15 pages).
Echigo, Ryosuke et al.; "Rat Daigae Domyaku Model o Mochiita Trehalose ni yoru Kekkan Renshuku no Yokusei Koka"; Annual Meeting of the Japan Neurosurgical Society Abstract; Abstract No. 2K-P30-7-9; 2007 (2 pages).

* cited by examiner

*Primary Examiner* — Lawrence E Crane
(74) *Attorney, Agent, or Firm* — Osha Liang LLP

(57) ABSTRACT

An object of the present invention is to provide an agent for treating or preventing vasospasm. An object of the present invention is to provide an agent for treating or preventing cerebral vasospasm as well as arterial vasospasm. Further, an object of the present invention is to provide an agent for treating or preventing cerebral ischemia and cerebral infarction.
The above problems are solved by an agent for treating and preventing vasospasm, cerebral ischemia, or cerebral infarction, comprising trehalose as the active ingredient. It is possible, by using such a trehalose-comprising agent, to suppress phenomena such as contraction of blood vessel and thickening of tunica intima and tunica media and to prevent or treat vasospasm and vasospasm-dependent diseases.

4 Claims, 13 Drawing Sheets

THERAPEUTIC OR PROPHYLACTIC AGENT FOR VASOCONSTRICTION

BACKGROUND OF THE INVENTION

1. Field of the Invention

The present invention relates to an agent comprising trehalose for preventing or treating vasospasm, cerebral ischemia or cerebral infarction.

2. Description of the Related Art

Subarachnoid hemorrhage (SAH) is a disease in which there is bleeding in subarachnoidal space. Patients with subarachnoid hemorrhage also often develop, for example, consciousness disturbance, possibly resulting in death.

A symptom developing after subarachnoid hemorrhage is cerebral vasospasm. Cerebral vasospasm is a disease wherein constriction of a cerebral vessel develops within two weeks after subarachnoid hemorrhage. Patients with cerebral vasospasm exhibit cerebral ischemia symptom and may go into a vegetable state or even die. However, the action mechanism and the causative substances of cerebral vasospasm are yet to be elucidated. For that reason, there exists a need for studies on the action mechanism and the causative substances of cerebral vasospasm and the development of an agent for treating or preventing cerebral vasospasm.

Oxyhemoglobin is suggested to cause cerebral vasospasm in R. Loch, et. al., "A Review of Hemoglobin and the Pathogenesis of Cerebral Vasospasm" Stroke, Vol. 22, No. 8, pp. 971-982. 1991.

Correlation between HO1 (Heme Oxygenases-1) and cerebral vasospasm is suggested in Minoru Kuroki, et al., "Effect of Vasospasm on Heme Oxygenases in Rat Model of Subarachnoid Hemorrhage".

Nimodipine, a Ca antagonist, is recommended for prevention of cerebral vasospasm in Mayberg, M. R., et al., "Guidelines for the Management of Aneurismal subarachnoid Hemorrhage" Circulation., Vol. 90, No. 5, pp. 2592-2605, 1994 (Non-Patent Document 1) (p. 2599, left column, lines 11 to 32).

An "agent for treating cerebral vasospasm characterized by comprising activated protein C as the active ingredient" is disclosed in JP-A No. 2000-247904 (Claim 1).

An agent for preventing or treating vasospasm comprising "(2R,4R)-4-methyl-1-[N2((RS)-3-methyl-1,2,3,4-tetrahydro-8-quinolinesulfonyl)-L-arginyl]-2-piperidinecarboxylic acid, the hydrate or a pharmaceutically acceptable salt thereof as the active ingredient is disclosed in JP-A No. 2000-086518 (Claim 1).

A "cerebral vasospasm inhibitor comprising alacepril as the active ingredient" is disclosed in JP-A No. 11-222439 (Claim 1). Alacepril is a known compound having a chemical name of "1-(D-3-acetylthio-2-methylpropanoyl)-L-prolyl-L-phenylalanine or (S)—N-[1-[3-(acetylthio)-2-methyl-1-oxopropyl]-L-prolyl]-L-phenylalanine".

An "agent for treating cerebral vasospasm characterized by comprising a thrombomodulin-like protein as the active ingredient" is disclosed in JP-A No. 09-025239 (Claim 1). The thrombomodulin-like protein means thrombomodulin, a peptide having a region of amino acid sequence that is essential for the biological or immunological activity of thrombomodulin, or the analogue thereof. The thrombomodulin-like protein is a protein substance that binds to thrombin, thus inhibiting thrombin's clotting-accelerating action and also accelerating activation of protein C by thrombin significantly.

An "agent for preventing, treating or alleviating cerebral vasospasm comprising 1-ethyl-2-[N-(2-methoxy)benzoyl-N-{2-methoxy-3-(4-octadecyl carbamoyloxy) piperidinocarbonyloxypropoxy}carbonyl]aminomethylpyridinium chloride or a pharmacologically acceptable salt thereof" is disclosed in JP-A No. 08-26994 (Claim 3).

A "cerebral vasospasm inhibitor characterized by comprising Maxadilan exhibiting vasodilating action to mammals" is disclosed in JP-A No. 07-173072 (Claim 1).

An "agent for preventing or treating cerebral vasospasm, comprising at least one peptide selected from calcitonin gene-dependent peptides and vasoactive intestinal polypeptides and urokinase in combination as the active ingredients" is disclosed in JP-A No. 06-116166 (Claim 1). The calcitonin gene-dependent peptide is abbreviated as CGRP and the vasoactive intestinal polypeptide, as VIP.

A thromboxane synthase inhibitor "Sodium Ozagrel Intravenous Infusion" 80 mgJD is sold from Nippon Hexal Corporation. The medicine is said to suppress cerebral vasospasm and alleviates cerebral ischemia and movement disturbance associated with cerebral thrombosis.

As described above, various agents for treating or preventing cerebral vasospasm have been proposed, but there is no highly effective medicine available yet.

On the other hand, vasospasm induces diseases other than those by cerebral vasospasm, such as cerebral ischemia and cerebral infarction. For example, if an abnormal phenomenon occurs on blood vessel such as breakage of blood vessel in case of placement of catheter, transplantation of blood vessels such as formation of bypass blood vessels, and placement of a stent or an embolization coil in addition to a normal surgical operation, it may induce vasospasm. This vasospasm makes difficult the surgical operation, insertion of a catheter, placement of a stent, etc. It is possible to improve the safety of an operation, if the vasospasm during a surgical operation of blood vessels, for example, during bypass blood vessel formation, can be prevented. It is also possible to improve the safety of an operation or placement of a stent, if the vasospasm during insertion of a catheter and before placement of a stent or an embolization coil can be prevented. Accordingly, there exists a need for an agent for preventing the vasospasm associated with a transvascular operation.

Alternatively, tension caused by a vascular transplant, a catheter, a stent or an embolization coil may induce vasospasm. For example, vasospasm caused by coronary artery transplant may cause obstruction of blood vessel and even myocardial infarction. For that reason, there exists a need for an agent for treating vasospasm associated with a vascular transplant operation such as a transvascular operation that breaks blood vessels or applies external force to blood vessels and also for an agent for preventing or treating vasospasm after placement of a catheter, a stent or an embolization coil. That is, prevention of vasospasm after a surgical operation such as vascular transplantation paves the way to prevention of severe diseases such as heart diseases including myocardial infarction. Thus, there is a demand for an agent for treating, preventing, or alleviating vasospasm caused by a surgical operation.

"Use of (-)-[[4-(1,4,5,6-tetrahydro-4-methyl-6-oxo-3-pyridazinyl)phenyl]hydrazono]-propanedinitrile or a pharmaceutically acceptable salt thereof in production of an agent for treating or preventing vasospasm by coronary artery transplant" is disclosed in Japanese Patent Application National Publication No. 2003-503353.

Development of a slow-release cerebral vasospasm inhibitor for intracerebral implant is also desired. Slow-release cerebral vasospasm inhibitors comprising a water-soluble polymer having a cellulose skeleton and sugars as the slow-release carrier are disclosed, for example, in JP-A No. 7-267880 (Patent Document 2) (Claim 18). It is described in the same document (paragraph [0010]), "Examples of the sugars used include sucrose, lactose, glucose, fructose, maltose, dextrin, trehalose, pullulan and the like. Among them, lactose and glucose are preferable. It is possible to adjust the slow-release velocity by addition of sugars, and the addition in a greater amount leads to increase in release velocity". Thus in the same document, trehalose is cited as a sugar controlling the drug release velocity of the slow-release carrier water-soluble polymer. However, there is no example actually employing trehalose or no description on the efficacy of trehalose at all. In the same document, there is no description of trehalose's action to treat or prevent vasospasm at all.

Alternatively, a blood circulation improver comprising glycosylated vitamin P as the active ingredient is disclosed in JP-A No. 11-171778 (Claim 1). A blood circulation improver comprising a glycosylated vitamin P as the active ingredient and trehalose additionally is also disclosed in the same document (Claim 5). Disclosed in the same document is that trehalose intensifies the blood circulation-improving action of the glycosylated vitamin P (for example, paragraph [0009]). In the document, the glycosylated vitamin P having blood circulation-improving action is a major agent, and trehalose is described only as an additional agent intensifying the blood circulation-improving action of the glycosylated vitamin P. There is no description of trehalose's action to treat or prevent vasospasm in the same patent document.

Alternatively, JP-A No. 2002-161049 (Patent Document 3 below) discloses a vascular intima-thickening inhibitor comprising epidermal growth factor family as the active ingredients. The paragraph [0031] teaches, "The solid preparation can be prepared as freeze-drying substances by adding an excipient such as mannitol, trehalose, sorbitol, lactose, glucose, maltose, saccharose, starch, or magnesium stearate to epidermal growth factor EGF. It may be powdered." In other words, trehalose is cited as a diluent for production of the solid preparation. However, trehalose is exemplified only as a diluent, and there is no example actually using trehalose or no description about the efficacy of trehalose at all. The same document does not describe trehalose's action to treat or prevent vasospasm at all.

Patent Document 1: JP-A No. 2000-247904
Patent Document 2: JP-A No. 7-267880
Patent Document 3: JP-A No. 2002-161049
Non-Patent Document 1: Mayberg, M. R., et al., "Guidelines for the Management of Aneurismal subarachnoid Hemorrhage" Circulation., Vol. 90, No. 5, pp. 2592-2605, 1994

SUMMARY OF THE INVENTION

Problems to be Solved by the Invention

An object of the present invention is to provide an agent for treating or preventing vasospasm. Another object of the present invention is to provide an agent for treating or preventing cerebral vasospasm as well as vasospasm possibly inducing heart diseases, and other diseases.

Yet another object of the present invention is to provide an agent for treating or preventing cerebral ischemia.

Yet another object of the present invention is to provide an agent for treating or preventing cerebral infarction.

Means for Solving Problems

The present invention is, fundamentally based on the experiments showing that it is possible to suppress phenomena such as constriction of blood vessel and thickening of tunica intima and tunica media by using an agent comprising trehalose. As will be demonstrated in Examples below, use of a trehalose-comprising agent permits effective inhibition of vasospasm. Thus, the agent according to the present invention, which contains trehalose, can prevent or treat vasospasm and vasospasm-dependent diseases.

A first aspect of the present invention relates to an agent for treating or preventing vasospasm, comprising trehalose as the active ingredient.

A preferred embodiment of the first aspect of the present invention relates to the agent for treating or preventing vasospasm, comprising trehalose in an amount of from 5 wt % to 40 wt %, both inclusive, which is used for intravascular administration.

A preferred embodiment of the first aspect of the present invention relates to any one of the above agents for treating or preventing vasospasm, comprising trehalose in an amount of from 1 wt % to 15 wt %, both inclusive, which is used for extravascular administration.

A preferred embodiment of the first aspect of the present invention relates to any one of the above agents for treating or preventing vasospasm, comprising trehalose as well as glucose.

A preferred embodiment of the first aspect of the present invention relates to any one of the above agents for treating or preventing vasospasm, comprising trehalose as well as hemoglobin-based oxygen carrier or a perfluorocarbon.

A preferred embodiment of the first aspect of the present invention relates to any one of the above agents for treating or preventing vasospasm, comprising trehalose as well as one or more compounds selected from the group consisting of "endothelin receptor antagonists, vasodilators, thrombolytic agents, cerebral circulation-improving agents, and cerebral vasospasm-inhibiting substances other than trehalose," pharmaceutically acceptable salts thereof, or solvated derivatives thereof.

A preferred embodiment of the first aspect of the present invention relates to any one of the above agents for treating or preventing vasospasm that is a perfusion agent.

A preferred embodiment of the first aspect of the present invention relates to any one of the above agents for treating or preventing vasospasm, wherein the vasospasm is cerebral vasospasm.

A preferred embodiment of the first aspect of the present invention relates to any one of the above agents for treating or preventing vasospasm that is an agent for treating or preventing cerebral ischemia.

A preferred embodiment of the first aspect of the present invention relates to any one of the above agents for treating or preventing vasospasm that is an agent for treating or preventing cerebral infarction.

A preferred embodiment of the first aspect of the present invention relates to any one of the above agents for treating or preventing vasospasm that is an agent for treating or preventing heart diseases.

A preferred embodiment of the first aspect of the present invention relates to the agent for treating or preventing vasospasm, which is an agent for treating or preventing vasospasm associated with a transvascular operation. As will be demonstrated in Examples below, trehalose can inhibit vasospasm effectively. As will be demonstrated in Examples below, trehalose also exhibits anti-inflammatory action. Use of a trehalose-comprising agent can effectively inhibit vasospasm induced by a surgical operation and also inflammatory reactions. Thus, it can be used as an anti-inflammatory agent during an operation.

A preferred embodiment of the first aspect of the present invention relates to any one of the above agents for treating or preventing vasospasm, which is an agent for treating or preventing vasospasm associated with microsurgery of blood vessels.

A preferred embodiment of the first aspect of the present invention relates to any one of the above agents for treating or preventing vasospasm for prevention of vasospasm before placement of stent or embolization coil or for treatment or prevention of vasospasm after placement of a stent or an embolization coil.

EFFECT OF THE INVENTION

As will be demonstrated in Examples below, the agent according to the present invention comprising trehalose as the active ingredient is effective for treatment and prevention of vasospasm. Accordingly, the present invention provides an agent for treating or preventing vasospasm. As will be demonstrated in Examples below, the agent according to the present invention is also effective for treatment and prevention of vasospasm when used in femoral artery. Thus, the present invention provides an agent for treating or preventing vasospasm possibly inducing heart diseases and others. It is possible to prevent vasospasm effectively by using the agent as a perfusion agent, especially as a perfusion agent comprising trehalose in a particular amount.

Vasospasm induces ischemia such as cerebral ischemia. The agent according to the present invention, which treats or prevents vasospasm, can prevent ischemia and can also be used as an improver preventing progress of ischemia. The improver will be effective for treatment of ischemia. Thus, the present invention provides an agent for treating or preventing ischemia such as cerebral ischemia.

Vasospasm induces cerebral infarction. The agent according to the present invention, which treats or prevents vasospasm, can prevent cerebral infarction and can also be used as an improver preventing progress of cerebral infarction. The improver is effective for treatment of cerebral infarction. The present invention provides an agent for treating or preventing cerebral infarction.

Vasospasm induces heart diseases such as myocardial infarction and ischemic states by hematogenous disorder in coronary artery. The agent according to the present invention, which treats or prevents vasospasm, prevents heart diseases and can also be used as an improver preventing progress of the heart diseases. The improver will be effective for treatment of the heart diseases. The present invention provides an agent for treating or preventing heart diseases.

As will be demonstrated in Examples below, the agent according to the present invention comprising trehalose as the active ingredient exhibits anti-inflammatory action. Thus, the agent according to the present invention can be used as an agent for preventing or treating vasospasm possibly induced by a surgical operation, specifically not only by a normal surgical operation, but also during placement of a catheter, during a vascular transplantation operation for example for formation of bypass blood vessels, and during placement of a stent or an embolization coil, and also as an anti-inflammatory agent.

DETAILED DESCRIPTION OF THE PREFERRED EMBODIMENTS

Figure 1:
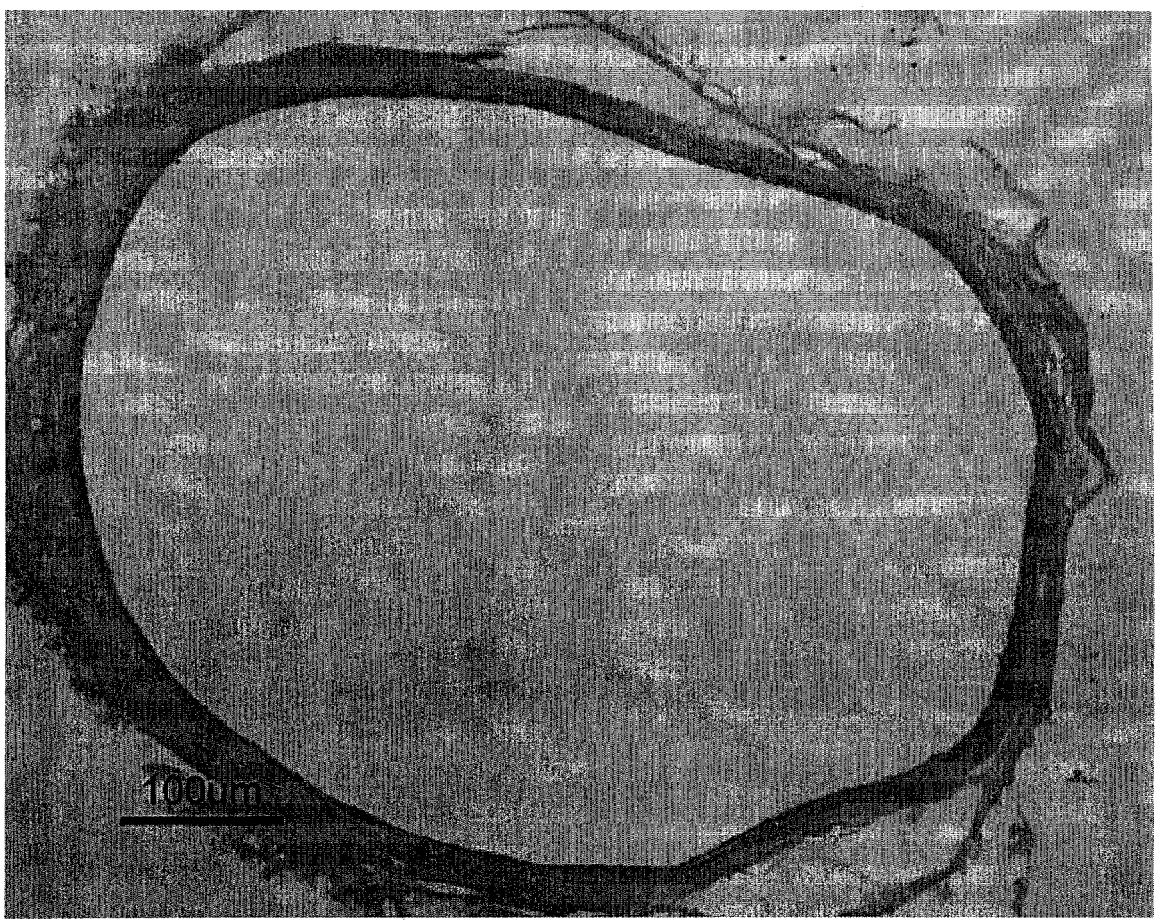
FIG. 1 is a photograph replacing a drawing, showing a tissue image of the right femoral artery of control.

1. Agent According to the Present Invention

A first aspect of the present invention relates to an agent for treating or preventing vasospasm, comprising trehalose as the active ingredient (agent according to the present invention). The therapeutic agent means an agent for treatment or alleviation of a particular disease. The preventive agent means an agent for prevention of affection of a particular disease.

The content of trehalose may be adjusted properly according to application, form of formulation, patient, and others. As will be demonstrated in Examples below, if the agent according to the present invention is a liquid formulation for intravascular administration, the content of trehalose is preferably from 5 wt % to 40 wt %, both inclusive, in the agent, and more preferably, it is administered in an amount adjusted to an intravascular trehalose concentration of from 2 wt % to 7 wt %, both inclusive. Alternatively, in the case of extravascular administration, if the agent according to the present invention is a liquid formulation, the content of trehalose is preferably from 1 wt % to 15 wt %, both inclusive, in the agent, more preferably from 2 wt % to 10 wt %, both inclusive, in the agent, and still more preferably, it is administered in an amount adjusted to a trehalose concentration of from 3 wt % to 7 wt %, both inclusive, at the administration site. If the agent according to the present invention is a solid formulation, the content of trehalose is preferably in the above range after the agent according to the present invention is dissolved in solvent. There are three kinds of trehalose isomers different from one another in bonding pattern: α,α isomer, α,β isomer and β,β isomer. In the present invention, the production method, purity and properties of the agent are not limited, if the agent contains one or more isomers of these in an effective amount as a whole.

Examples of "vasospasm" include cerebral vasospasm, arterial vasospasm, vasospasm associated with a transvascular operation such as bypass surgery and catheter insertion, and vasospasm associated with placement of a stent or an embolization coil (in particular, an arterial embolization coil). As will be demonstrated in Examples below, the agent according to the present invention can also prevent or treat arterial vasospasm other than cerebral vasospasm such as femoral artery. Examples of the arterial vasospasm include cerebral vasospasm, vasospasm of aorta as well as coronary artery, hepatic artery, and femoral artery, and others. Thus, vasospasm induces cerebrovascular diseases as will be described below and also other diseases such as heart disease. For example, coronary diseases are induced by constriction of vascular lumen caused by pultaceous arteriosclerosis (atherosclerosis) and also by the ischemic state caused by hematogenous disorder of coronary artery by vasospasm. Vasospasm is also a factor responsible for myocardial infarction. Thus, the agent according to the present invention, which treats or prevents vasospasm of coronary artery and others, is effective also as an agent for treatment or prevention of heart diseases such as coronary disease and myocardial infarction. The agent according to the present invention, which is considered to be effective to vasospasm in general, can also effectively treat and prevent vasospasm associated with a transvascular operation and vasospasm associated with placement of a stent or an embolization coil.

For example, vasospasm due to cerebral vasospasm induces cerebral ischemia. For that reason, the agent according to the present invention preferably contains glucose in addition to trehalose as the active ingredient. The content of glucose may be similar to that in normal glucose infusion, for example, from 0.1 wt % to 80 wt %, both inclusive, or possibly from 0.5 wt % to 10 wt %, both inclusive, in the drug solution. The ratio by weight of trehalose to glucose may be arbitrary, and trehalose may be used, for example, in an amount of from 0.1 times to 20 times, both inclusive, of glucose. Thus, such an agent can prevent or treat vasospasm with trehalose and also ischemia following the progress of the symptom.

Ischemia, once induced by vasospasm, prohibits sufficient transportation of nutrition to body cells, possibly causing cell death. Cell death of cerebral cells caused by ischemia may lead to development of cranial nerve disorder. It is possible to prevent or treat the ischemia-causing vasospasm, by administering an agent comprising trehalose as an active ingredient, as in the present invention. It is in this way possible to prevent or treat ischemia. It is thus possible to prevent or treat cranial nerve disorder by preventing or treating vasospasm-derived ischemia with the agent according to the present invention.

From the same viewpoint as above, the agent according to the present invention preferably contains, in addition to trehalose, a hemoglobin-based oxygen carrier or a perfluorocarbon. The contents of the hemoglobin-based oxygen carrier and the perfluorocarbon in the agent according to the present invention may be adjusted properly, and are not particularly limited. The content of the hemoglobin-based oxygen carrier is, for example, a concentration of from 0.5 times to 2 times, both inclusive, of the concentration by weight of hemoglobin contained in the blood of able-bodied people. More specific concentration is, for example, from 0.1 to 10 g, both inclusive, Hb/dl in blood, and from 0.5 times to 1.1 times, both inclusive, by weight of the hemoglobin contained in the lost blood if the blood is lost, for example, by a surgical operation. The content of the perfluorocarbon is a concentration determined according to the symptom and application, and for example, from 0.01 wt % to 10 wt %, both inclusive, in the agent according to the present invention. Further, specific dosage of the perfluorocarbon is also adjusted properly according to symptom and application, and specifically, it is from 0.1 mg to 40 mg both inclusive, per kg of body weight. That is, such an agent can prevent or treat vasospasm with trehalose and also ischemia, which may occur after the progress of the symptom.

Those described, for example, in Japanese Patent Application National Publication No. 2004-536368 and JP No. 2962731 or the corresponding U.S. patents can be appropriately used as the hemoglobin-based oxygen carriers. These documents are incorporated herein by reference. The hemoglobin-based oxygen carrier is, for example, a hemoglobin-based oxygen carrier of synthetic hemoglobin, synthetic hemoglobin analogue, liposome-encapsulated hemoglobin, chemically modified hemoglobin, or crosslinked hemoglobin molecule.

Known perfluorocarbons that are used in synthetic bloods can be appropriately used as the perfluorocarbons. Those described, for example, in Japanese Patent Application National Publication No. 2003-522094, Japanese Patent Application National Publication No. 2000-516569 and Japanese Patent Application National Publication No. 10-505319 or the corresponding U.S. patents can be appropriately used as the perfluorocarbons. These documents are incorporated herein by reference. Preferable perfluorocarbons include $C_{10}$ perfluorocarbons, anymore preferable perfluorocarbons include compounds comprising a cyclopentyl or cyclohexyl group, and all hydrogen atoms on the ring and the substituent group of which are substituted with fluorine atoms. Examples thereof include perfluoro-1,2,3,4-tetramethylcyclohexane, perfluoro-1,2,4,5-tetramethylcyclohexane, perfluoro-1,2,3,5-tetramethylcyclohexane, perfluoro-1,2-dimethyl-3-ethylcyclohexane, perfluoro-1,2-dimethyl-4-ethylcyclohexane, perfluoro-1,3-dimethyl-2-ethylcyclohexane, perfluoro-1,3-dimethyl-4-ethylcyclohexane, perfluoro-1,3-dimethyl-5-ethylcyclohexane, perfluoro-1,4-dimethyl-2-ethylcyclohexane, perfluoro-n-butylcyclohexane, perfluoro-(2-methylpropyl)cyclohexane, perfluoro-(1-methylpropyl)cyclohexane, perfluoro-t-butylcyclohexane, perfluoro-1,1-diethylcyclohexane, perfluoro-1-methyl-1-n-propylcyclohexane, perfluoro-1-methyl-1-iso-propylcyclohexane, perfluoro-1-pentylcyclopentane, perfluoro-1-methyl-1-butylcyclopentane, perfluoro-1-ethyl-1-propylcyclopentane, and perfluoro-neopentylcyclopentane.

2. Conjunctive Agent

The active ingredient in the agent according to the present invention is trehalose. However, the agent according to the present invention may contain an additional agent (a conjunctive agent) as described below as needed. Examples of the conjunctive agents include Fasudil, endothelin receptor antagonists, vasodilators, thrombolytic agents, cerebral circulation-improving agents, and cerebral vasospasm-inhibiting substances other than trehalose. That is, the agent according to the present invention may contain, in addition to the active ingredient trehalose, one or more compounds selected from the group consisting of "Fasudil, endothelin receptor antagonists, vasodilators, thrombolytic agents, cerebral circulation-improving agents, and cerebral vasospasm-inhibiting substances other than trehalose" or the pharmaceutically acceptable salts or the solvated derivatives thereof.

The pharmaceutically acceptable salts are, for example, salts with a mineral acid such as sulfuric acid, hydrochloric acid, or phosphoric acid, salts with an organic acid such as acetic acid, oxalic acid, lactic acid, tartaric acid, fumaric acid, maleic acid, methanesulfonic acid, or benzenesulfonic acid, salts with an amine such as trimethylamine or methylamine, salts with a metal ion such as sodium ion, potassium ion or calcium ion, and the like. In the case of a compound comprising water by change over time, the water is also included in the pharmaceutically acceptable salts.

The solvated derivatives include pharmaceutically acceptable solvated derivatives, and specific examples include hydrates. The hydrates include known hydrates such as semihydrate, monohydrate, and trihydrate. Some of the conjunctive agents according to the present invention have stereoisomers, geometrical isomers, optical isomers and others, and in the present invention, the conjunctive agent may contain such isomers as needed. The agents according to the present invention also include solvated derivatives and simultaneously salts of a compound.

2.1. Fasudil

It is reported that intravenous administration of Fasudil hydrochloride, a myosin light-chain phosphorylating enzyme activity inhibitor, is effective in systemic pharmaceutical therapy to tardive cerebral vasospasm (Shibuya, et. al, J. Neurosurg. 1992, 76, 571-577). Accordingly, the agent according to the present invention preferably contains Fasudil as the conjunctive agent. Fasudil, which has a compound name of 1-(5-isoquinolinesulfonyl)homopiperazine, is described, for example, in JP-A No. 61-227581 (U.S. Pat. No. 4,678,783). In addition to the Fasudil hydrochloride salt, the semihydrate, the 3/2 hydrate, and the hydrate hydrochloride thereof are known, and these may be used as needed in the present specification. The Fasudil hydrochloride hydrate is known as a vasodilator, and used for alleviation of the cerebral vasospasm after a surgical operation of subarachnoid hemorrhage and the associated cerebral ischemia symptoms.

2.2. Endothelin Receptor Antagonist

Katsutoshi Goto reports in his article, "Development of endothelin receptor antagonist-converting enzyme inhibitors," Biomedicine & Therapeutics August 2004 that endothelin receptor antagonists having a sulfonamide skeleton especially was demonstrated to exhibit distinctive advantageous effects in various animal disease models (acute renal failure by ischemia, cerebral vasospasm by intraventricular administration of own blood, thickening of carotid artery by balloon damage, nerve death in the hippocampus C1 region by ischemia, etc.). Thus, the agent according to the present invention preferably contains an endothelin receptor antagonist as the conjunctive agent. Examples of the endothelin receptor antagonists include bosentan, tezosentan, darusentan, atrasentan, enrasentan, sitaxsentan, and the pharmaceutically acceptable salts thereof.

2.3. Vasodilator

Examples of the vasodilators include Fasudil described above, calcium antagonists, papaverine, statins, nitroglycerin, isosorbit nitrate, diltiazem, nicorandil, the pharmaceutically acceptable salts thereof, and the like. A Ca antagonist nimodipine is recommended for prevention of cerebral vasospasm, for example, in Mayberg, M. R., et al., "Guidelines for the Management of Aneurismal subarachnoid Hemorrhage" Circulation., Vol. 90, No. 5, pp. 2592-2605, 1994 (Non-Patent Document 1). Thus, the agent according to the present invention preferably contains a vasodilator, preferably a calcium antagonist vasodilator, as the conjunctive agent. Examples of the calcium antagonists include nimodipine or the pharmaceutically acceptable salts thereof, as well as efonidipine hydrochloride, diltiazem hydrochloride, nicardipine hydrochloride, benidipine hydrochloride, verapamil hydrochloride, nisoldipine, nitrendipine and the like.

Statins are present in the pro-drug lactone form and in the acid form in the body. And, the acid-form statins all have 3,5-dihydroxyvaleric acid (DHVA) and other hydrophobic regions. A DHVA-like structure is found in substrates for HMG-CoA reductase and the reaction intermediates thereof. Thus, any statin functions as a HMG-CoA reductase inhibitor. On the other hand, statins are known to have vasodilating action and angiogenesis-accelerating action (Kureishi, et. al. "The HMG-COA reductase inhibitor simvastatin activates the protein kinase Akt and promotes angiogenesis in normocholesterolemic animal." Nature Med. 200, 6, 1004-1010). Thus, the agent according to the present invention preferably contains a statin compound (in particular, simvastatin) as the conjunctive agent.

Typical examples of the statin compounds include mevastatin (ML-236B) disclosed in JP-A No. 50-155690, lovastatin (Monacolin K) disclosed in JP-A No. 56-40610, simvastatin disclosed in JP-B No. 64-1476 (and U.S. Pat. No. 4,444,784), bravastatin disclosed in JP-B No. 61-13699, fluvastatin disclosed in JP No. 2774035, atorvastatin disclosed in JP-B No. 7-57751 (U.S. Pat. No. 4,681,893) and the like.

2.4. Thrombolytic Agent

Examples of the thrombolytic agents include urokinase-type plasminogen activator (u-PA), tissue plasminogen activator (t-PA), and urokinase (UK), and the like. If a thrombolytic agent is used as the conjunctive agent, the agent according to the present invention is preferably used for intracisternal administration. Fibrinogenolytic therapy by using a thrombolytic agent such as urokinase is currently carried out for dissolution of thrombus. A freeze-dried thrombolytic agent it is dissolved for example in physiological saline or glucose injection solution before use and is administered by intravenous injection or instillation.

2.5. Cerebral Vasospasm-inhibiting Substance

Known cerebral vasospasm-inhibiting substances include, for example, activated protein C, (2R,4R)-4-methyl-1-[N2 ((RS)-3-methyl-1,2,3,4-tetrahydro-8-quinolinesulfonyl)-L-arginyl]-2-piperidinecarboxylic acid, alacepril, thrombomodulin-like proteins, 1-ethyl-2-[N-(2-methoxy)benzoyl-N-{2-methoxy-3-(4-octadecyl carbamoyloxy) piperidinocarbonyloxypropoxy}carbonyl] aminomethylpyridinium, Maxadilan, calcitonin gene dependent peptides, Maxadilan, CGRP, VIP, (−)-[[4-(1,4,5,6-tetrahydro-4-methyl-6-oxo-3-pyridazinyl)phenyl]hydrazono]-propanedinitrile, argatroban, heparin, deferoxamine, methylprednisolone, nicorandil, nicaraven, magnesium sulfate, actinomycin D, 21-aminosteroid, isoproterenol, nimodipine, hydrocortisone, nifedipine, diltiazem, dilazep, teprotide, AA861, OKY1581, amyl nitrite, erythrityl tetranitrate, isosorbide dinitrate, nitroglycerin, pentaerythritol tetronitrate, vasopressin, bradykin, PACAP, SOD, catalase, bepridil, nadololol, felodipine, isradipine, verapamil, atenolol, metoprolol, propranolol, nicardipine, amlodipine, azelnidipine, diltiazem, papaverine, nicorandil, nifedipine, nitroglycerin, flunarizine and the pharmaceutically acceptable salts thereof if present. Preferable among these "cerebral vasospasm-inhibiting substances" are nicardipine, amlodipine, azelnidipine, and the pharmaceutically acceptable salts thereof.

2.6. Cerebral Circulation-improving Agent

Examples of the cerebral circulation-improving agents include kalliginogenase, tocopherol nicotinate, ibudilast, ifenprodil, dihydroergotoxin, nicergoline, ozagrel, trapidil, dextran, nizofenone and the like, or the pharmaceutically acceptable salts thereof. Ozagrel having thromboxane synthase-inhibiting action is preferable as the cerebral circulation-improving agent. Ozagrel inhibits aggregation of platelets by arachidonic acid and collagen, by inhibiting thromboxane synthase. It is known to alleviate cerebral vasospasm after a surgical operation of subarachnoid hemorrhage and the accompanying cerebral ischemia symptoms in this way (Frizzell R T, et al., Screening for ocular hemorrhages in patients with ruptured cerebral aneurysms: a prospective study of 99 patients. Neurosurgery 41 (3): 529-533).

The conjunctive agent in the agent according to the present invention is an optional component and may not be contained. Alternatively, the agent according to the present invention may contain one or more conjunctive agents instead. The ratio (by weight) of the conjunctive agent to trehalose in the agent according to the present invention is, for example, from $1 \times 10^{-6}$ to $1 \times 10^{-1}$, both inclusive, preferably from $5 \times 10^{-3}$ to $5 \times 10^{-2}$, both inclusive.

3. Agent for Treating or Preventing Cerebral Ischemia

Cerebral vasospasm leads to development of cerebral ischemia symptoms. Prevention or treatment of vasospasm with the agent according to the present invention also leads to prevention of cerebral ischemia. Thus, the present invention also provides a preventive agent to cerebral ischemia, comprising the agent according to the present invention. In addition, prevention or treatment of vasospasm by using the agent according to the present invention suppresses progress of cerebral ischemia and thus alleviates cerebral ischemia. Therefore, the present invention also provides an agent for treating cerebral ischemia, comprising the agent according to the present invention. The present invention also provides a method of treating or preventing cerebral ischemia, including a step of administering the agent according to the present invention to a subject. Further, the present invention can also provide use of the agent according to the present invention in production of an agent for treating or preventing cerebral ischemia.

4. Agent for Treating or Preventing Cerebral Infarction

Cerebral vasospasm leads to cerebral infarction. Treatment or prevention of vasospasm with the agent according to the present invention also leads to prevention of cerebral infarction. Thus, the present invention provides an agent for preventing cerebral infarction, comprising the agent according to the present invention. In addition, prevention or treatment of vasospasm with the agent according to the present invention leads to suppression of progress of cerebral infarction and thus alleviates cerebral infarction. Therefore, the present invention provides an agent for treating cerebral infarction, comprising the agent according to the present invention. Further, the present invention also provides a method of treating or preventing cerebral infarction, including a step of administering the agent according to the present invention to a subject. Further, the present invention also provides use of the agent according to the present invention in production of an agent for treating or preventing cerebral infarction.

5. Agent for Treating or Preventing Heart Diseases

Vasospasm induces heart diseases such as ischemic states and myocardial infarction caused by hematogenous disorder in coronary artery. The agent according to the present invention, which contains trehalose as the active ingredient, can treat or prevent vasospasm and thus, can prevent heart diseases and can also be used as an improver preventing the progress of heart diseases.

6. Agent for Treating or Preventing Vasospasm Associated with Transvascular Operation The agent according to the present invention, which contains trehalose as the active ingredient, can treat or prevent vasospasm and thus can be used as an agent for treating or preventing vasospasm associated with a transvascular operation. Transvascular operations include an operation for treatment and other purposes of blood vessels themselves as well as an operation for treatment and other purposes of other organs via blood vessels. The present invention also provides a method of treating or preventing vasospasm associated with a transvascular operation, including a step of administering the agent according to the present invention to a subject. A preferable embodiment of the present invention is an agent for treating or preventing vasospasm associated with microsurgery of blood vessels. Microsurgery means a surgical operation performed under microscope. Microsurgery, such as (micro)angiostomy, often leads to development of vasospasm, which in turn makes the operation difficult. On the other hand, it is difficult to administer an agent for treating or preventing vasospasm during microsurgery, because fine blood vessels are handled. Alternatively, trehalose, which is superior in biocompatibility, can effectively prevent vasospasm and is effective especially as an agent for treating or preventing vasospasm associated with microsurgery of blood vessels. The present invention also provides a method of treating or preventing vasospasm associated with microsurgery of blood vessels, including a step of administering trehalose to a subject.

7. Agent for Treating or Preventing Vasospasm Associated with Placement of Stent or Embolization Coil The agent according to the present invention, which contains trehalose as the active ingredient, can treat or prevent vasospasm, and thus can prevent vasospasm before placement of a stent or an embolization coil and also can treat or prevent vasospasm after placement of a stent or an embolization coil. Thus, the present invention also provides a method of placing a stent or an embolization coil, including administering the agent according to the present invention to a subject and then placing the stent or the embolization coil. In addition, the present invention also provides a method of treating or preventing vasospasm, including a step of administering the agent according to the present invention to a subject after placement of a stent or an embolization coil, for prevention of vasospasm associated with placement of the stent or the embolization coil or for treatment the vasospasm after placement of the stent or the embolization coil. In addition, the agent according to the present invention, which contains trehalose as the active ingredient, has anti-inflammatory action and thus can be used as an anti-inflammatory agent. Thus, it can be used as an agent for treating or preventing vasospasm during an operation or after an operation and also, as an anti-inflammatory agent for suppression of inflammatory reactions induced by an operation. It is further possible to prevent vasospasm by adding trehalose for example to a controlled drug-releasing stent or embolization coil, without administration of agents after placement of the stent or the embolization coil. It is also possible to suppress the inflammatory reactions induced by placement of a stent or an embolization coil.

8. Pharmaceutical Composition and Others

The agent according to the present invention can be as an agent or a medicinal composition, including the active ingredient trehalose in combination with one or more pharmaceutically acceptable carriers, excipients and diluents. In addition to trehalose, the conjunctive agents described above may be contained therein as needed. Examples of carriers, excipients or diluents include physiological saline, water, lactose, dextrose, fructose, sucrose, sorbitol, mannitol, polyethylene glycol, propylene glycol, starch, gums, gelatin, alginates, calcium silicate, calcium phosphate, cellulose, water syrup, methylcellulose, polyvinylpyrrolidone, alkyl para-hydroxybenzoates, talc, magnesium stearate, stearic acid, glycerin, and oils, such as sesame oil, olive oil and soy bean oil. Physiological saline is preferable among them.

The agent according to the present invention is formulated by a common preparative method into an oral or parenteral formulation such as tablet, pill, capsule, granule, powder, liquid formulation, emulsion, suspension, ointment, injection or skin patch. The formulation according to the present invention is preferably liquid or injection, and specifically, injection or perfusion solution is more preferable. For example, the liquid formulation is obtained, while trehalose, conjunctive agents, and diluents are blended and agitated properly. The liquid formulation thus obtained may be sealed in an ampoule, a prefilled syringe or a medicinal pack.

As for the dosage of the agent according to the present invention, trehalose is administered orally or parenterally in an amount of from 0.1 mg to 5 g, both inclusive, to an adult patient (60 kg) at a time, once or several times a day as divided. Vasospasm is also induced, for example, by contraction of vascular tunica media, and thus, intravascular administration, such as continuous intravascular administration using a catheter is preferable as an administration method according to the present invention. Alternatively, an agent comprising trehalose at a particular concentration may be preferably administered by perfusion or intravenous injection. Because vasospasm is caused by a surgical operation, the agent according to the present invention may be administered to the surgical site for protection of the cells at the surgical site and prevention of vasospasm. Trehalose may be administered in an amount similar to that described above in these cases as well. The dosage can be appropriately adjusted according to the kind of the disease to be treated, age of patient, body weight, symptoms and others.

If the targeted disease is a brain-related disease, specific administration methods include, for example, intracisternal administration during operation as well as perfusion therapy by using cisterna drainage, intravenous administration by instillation, and the like.

9. Use in Production of Agent

The present specification provides use of the agent according to the present invention in production of an agent for treating or preventing vasospasm. Each agent described above can be appropriately used as the agent according to the present invention.

10. Treatment Method

The present specification also provides a method of treating or preventing vasospasm, including a step of administering the agent according to the present invention to a subject. The subjects include humans and non-human mammals. The "step of administering the agent according to the present invention to a subject" is, for example, a step of administering the agent according to the present invention to the target affected region by perfusion. Each of the agents described above may be appropriately used as the agent according to the present invention.

Hereinafter, the present invention will be described specifically with reference to Examples. However, the present invention can be modified as needed within the range obvious to those skilled in the art from the disclosure in the present specification, and it should be understood that the present invention is not limited to the following Examples.

EXAMPLE 1

Construction of Vasospasm Model by Using Femoral Artery

Twenty seven male SD rats of 10 weeks of age were divided into three groups randomly. These rats were properly anesthetized. The groin was cut open and then the femoral artery was divided and separated sufficiently from the surrounding soft tissue etc. The femoral artery was covered with a catheter. The catheter used was a 10 mm-length vinyl chloride cylindrical catheter. Self blood collected from femoral vein was fed into the space between the catheter and vascular adventitia and the bottom face of the cylinder was sealed with an adhesive agent. The adhesive agent used was a cyanoacrylate-based adhesive agent. The operations above were carried out aseptically and surgically. Then, the surgical injury was closed. The lumen of the blood-exposed femoral artery narrowed and the tunica intima and tunica media thickened, after peaking in about 7 days after exposure. This model is a model according to "Nakamura et al., Japan Neurosurgical Society, Abstract of 49th Annual Meeting 199, 1990".

Left and right femoral arteries (FAs) of each rat were exposed to the substances shown in the following Table 1 by using the model above. 4% paraformaldehyde (PFA) solution was perfused, 7 days after commencement of exposure and each femoral artery was fixed and collected. The collected femoral artery (FA) was immersed in 4% PFA, and part of the femoral artery was immersed in sucrose solution and then embedded as frozen. A section of 5 μm in thickness was obtained with cryostat from the frozen femoral artery thus obtained. The section was subjected to hematoxylin-eosin staining (HE staining). The HE-stained sample was analyzed by using an image analyzer equipped with an image analysis program, and the sectional area of the lumen and the thickness of the tunica media in each tissue were determined. The radius of the blood vessel was determined from the peripheral length of the lumen of the blood vessel, and the lumen sectional area was calculated from it. In addition, the distance between the internal and external elastic layers was measured at four points, and the average thereof was determined, to obtain the thickness of the tunica media. There were cases when the blood vessel was cleaved or was not sufficiently fixed during analysis, and thus 6 samples, which were analyzed under favorable conditions, among 9 samples prepared in each group, were selected for collection of data.

TABLE 1

|  | Number of samples | Right FA | Left FA |
| --- | --- | --- | --- |
| Group I (control) | n = 9 | Only PS | Blood:PS = 3:1 (by volume) |
| Group II (TL3.75%) | n = 9 | Only PS | Blood:15% TL solution = 3:1 |
| Group III (TL 7.5%) | n = 9 | Only PS | Blood:30% TL solution = 3:1 |

In Table, TL means trehalose and PS, physiological saline.

Figure 2:
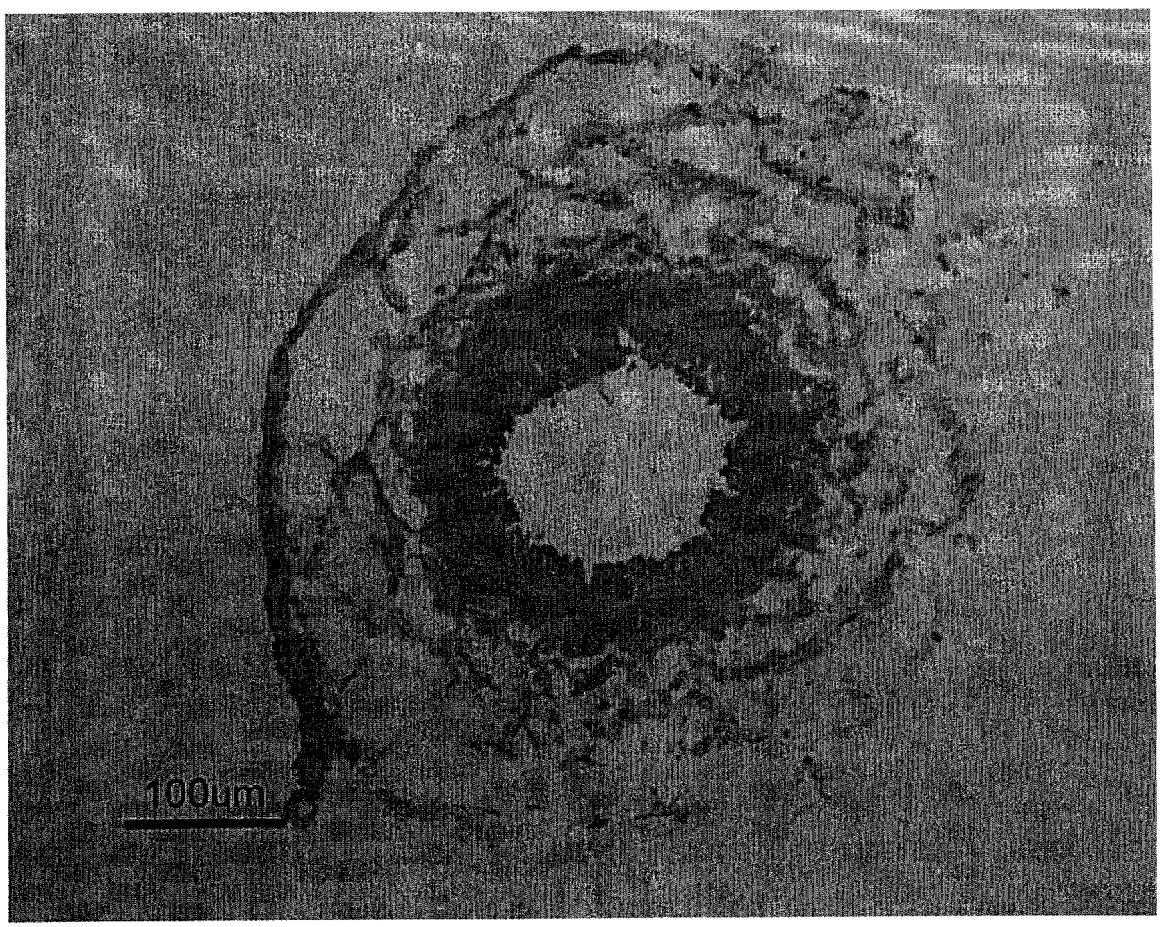
FIG. 2 is a photograph replacing a drawing, showing a tissue image of the left femoral artery in the same sample as in FIG. 1.

FIG. 1 is a photograph replacing a drawing, showing a tissue image of the right femoral artery of control. FIG. 2 is a photograph replacing a drawing, showing a tissue image of the left femoral artery in the same sample as FIG. 1. A comparison of the photographs in FIGS. 1 and 2 shows that exposure to blood leads to shrinkage of the blood vessel and contraction of the blood vessel.

Figure 3:
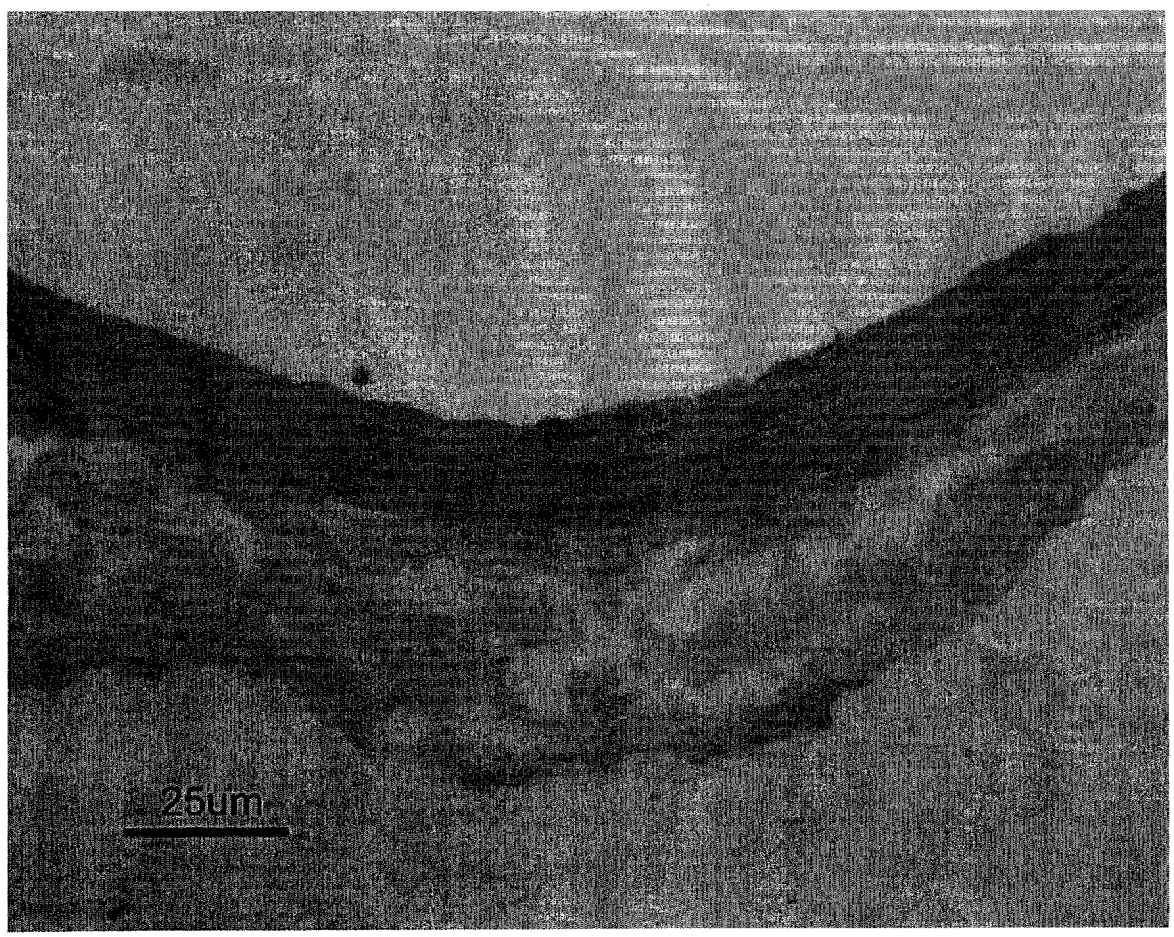
FIG. 3 is a photograph replacing a drawing, showing a tissue image of an artery having single-layered tunica intima and almost flattened tunica media cells.

FIG. 3 is a photograph replacing a drawing, showing a tissue image of an artery wherein the tunica intima is single-layered and the tunica media cells are also almost flat. FIG. 3 shows that the artery shown is a normal artery, the tunica intima is single-layered, and the tunica media cells are also almost flat.

Figure 4:
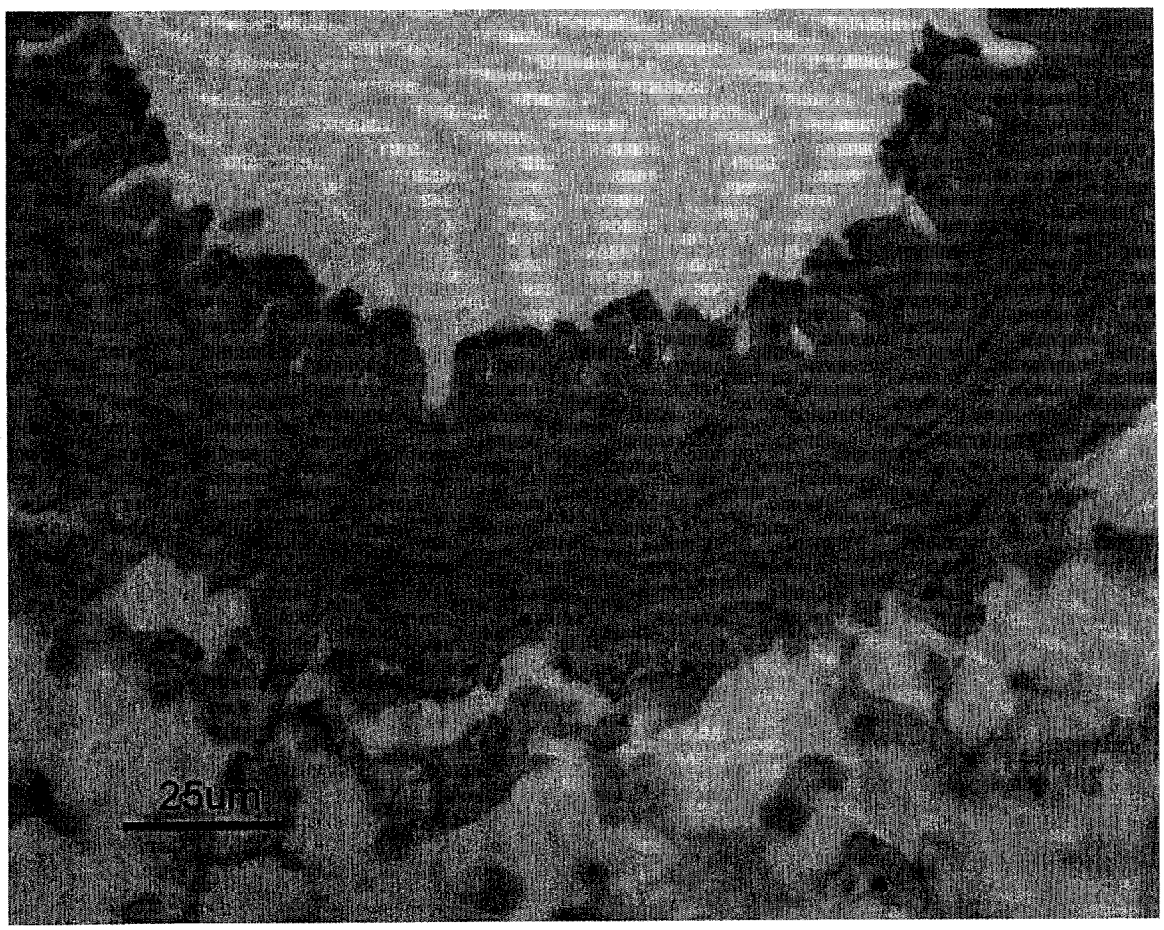
FIG. 4 is a photograph replacing a drawing, showing a tissue image of an artery with its tunica media severely thickened.

FIG. 4 is a photograph replacing a drawing, showing a tissue image of an artery wherein the tunica media are severely thickened. FIG. 4 shows that the tunica media in the artery shown is thickened and the internal elastic layer is roughened.

Figure 5:
FIG. 5 is a photograph replacing a drawing, showing a tissue image of an artery with its tunica intima cells severely proliferated.

FIG. 5 is a photograph replacing a drawing, showing a tissue image of an artery wherein the tunica intima cells are severely proliferated. FIG. 5 shows that the endothelial cells are proliferated and the tunica intima and the tunica media are thickened in the arterial wall.

Such tissue images were observed in all groups I, II and III with some variations.

Figure 6:
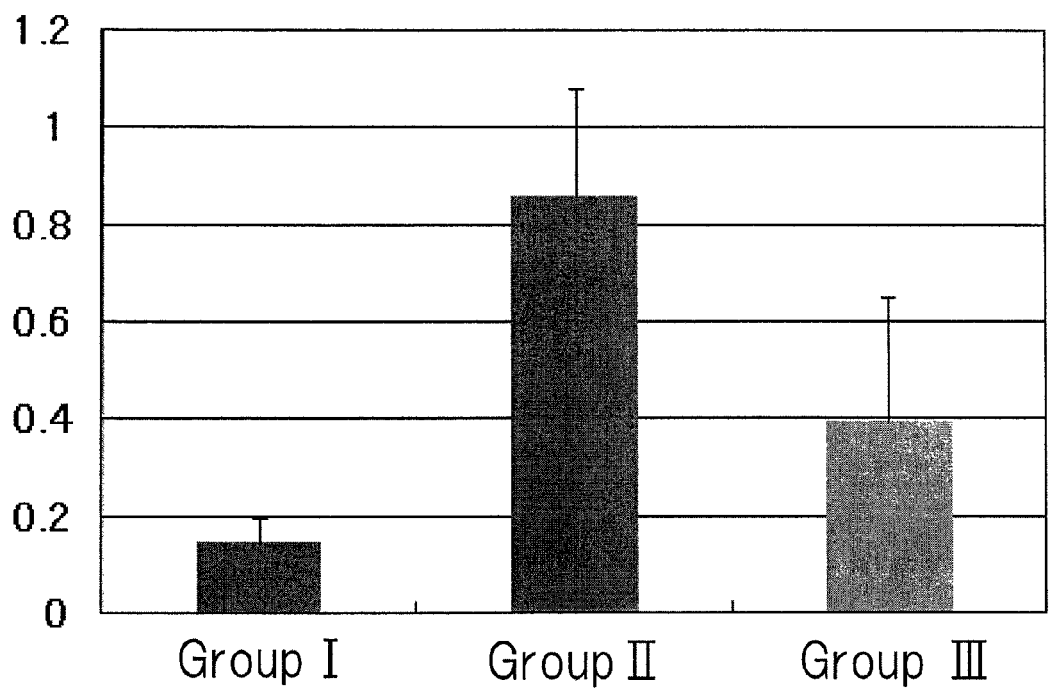
FIG. 6 is a graph showing the sectional area of lumens.

FIG. 6 is a graph showing the sectional area of the lumens. In the graph shown in FIG. 6, the ordinate shows the value of: [{sectional area of artery after exposure to blood (+trehalose)} /{sectional area of artery after exposure to physiological saline}]. Thus, smaller ordinate value means that the arterial sectional area (i.e., arterial diameter) is reduced by exposure to blood. FIG. 6 shows that the lumen diameter was reduced to 14% in group I (control, only with blood). On the other hand, FIG. 6 shows that the lumen diameter was 86% in group II (trehalose: 3.75 wt %), suggesting suppression of vasospasm. FIG. 6 also shows that the lumen diameter was reduced to 39% in group III (trehalose: 7.5 wt %). That is, a comparison of groups I and II demonstrates that administration of trehalose can suppress vasospasm. On the other hand, a comparison of groups II and III suggests that it is possible to suppress narrowing of blood vessels drastically by adjusting the content of trehalose contained in the agent.

Bonferroni/Dunn test was used as a statistical test for evaluation. As a result, p was <0.0001 (significant) between groups I and II; p was <0.0009 (significant) between groups II and III; and p was <0.0464 between groups I and III.

Figure 7:
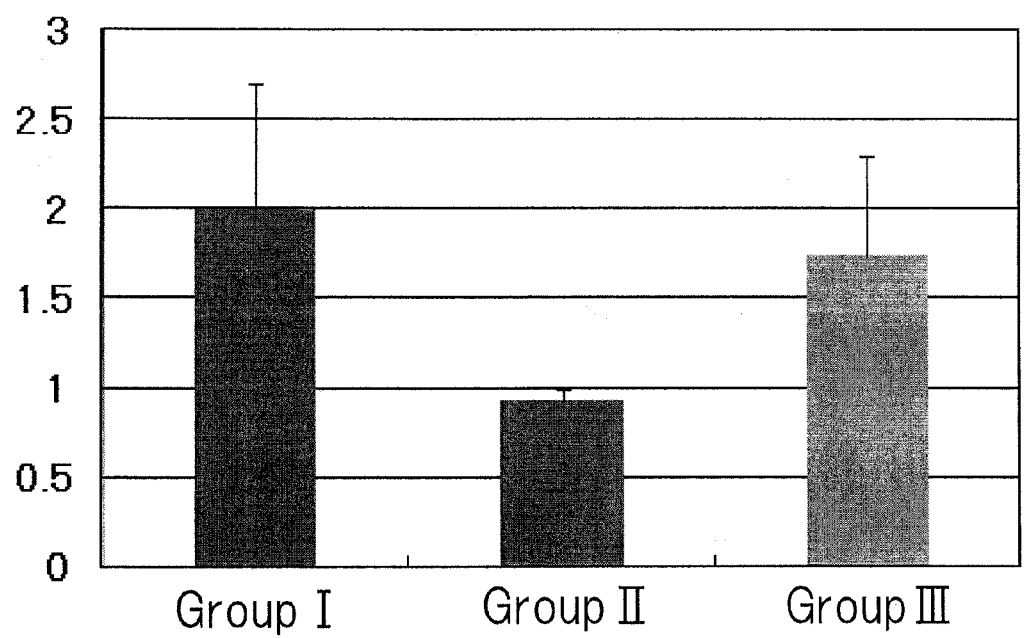
FIG. 7 is a graph showing the thickness of tunica media.

FIG. 7 is a graph showing the thickness of the tunica media. The ordinate in the graph of FIG. 7 shows the value: [{thickness of arterial tunica media after exposure to blood (+trehalose)}/{thickness of arterial tunica media after exposure to physiological saline}]. Thus, larger ordinate value means that the tunica media is thickened after exposure to blood. As shown in FIG. 7, the tunica media thickness was increased respectively by 2.0 times, 0.93 times, and 1.74 times in groups I, II and III. That is, a comparison of groups I and II shows that administration of trehalose can prevent increase in tunica media thickness. On the other hand, comparison of groups II and III shows that it is possible to prevent thickening of the tunica media effectively by adjusting the content of trehalose in the agent.

Bonferroni/Dunn test was used as a statistical test for evaluation. As a result, p was <0.0027 (significant) between groups I and II; p was <0.0163 (significant) between groups II and III; and p was <0.3929 between groups I and III.

EXAMPLE 2

Study (1) on the Inflammatory Action of Trehalose by Using Vasospastic Cell Model A vasospastic cell model was constructed by using rat macrophage-like cells (RAW264.7) for study on whether trehalose has anti-inflammatory action.

Method of Constructing of Vasospastic Cell Model

Figure 8:
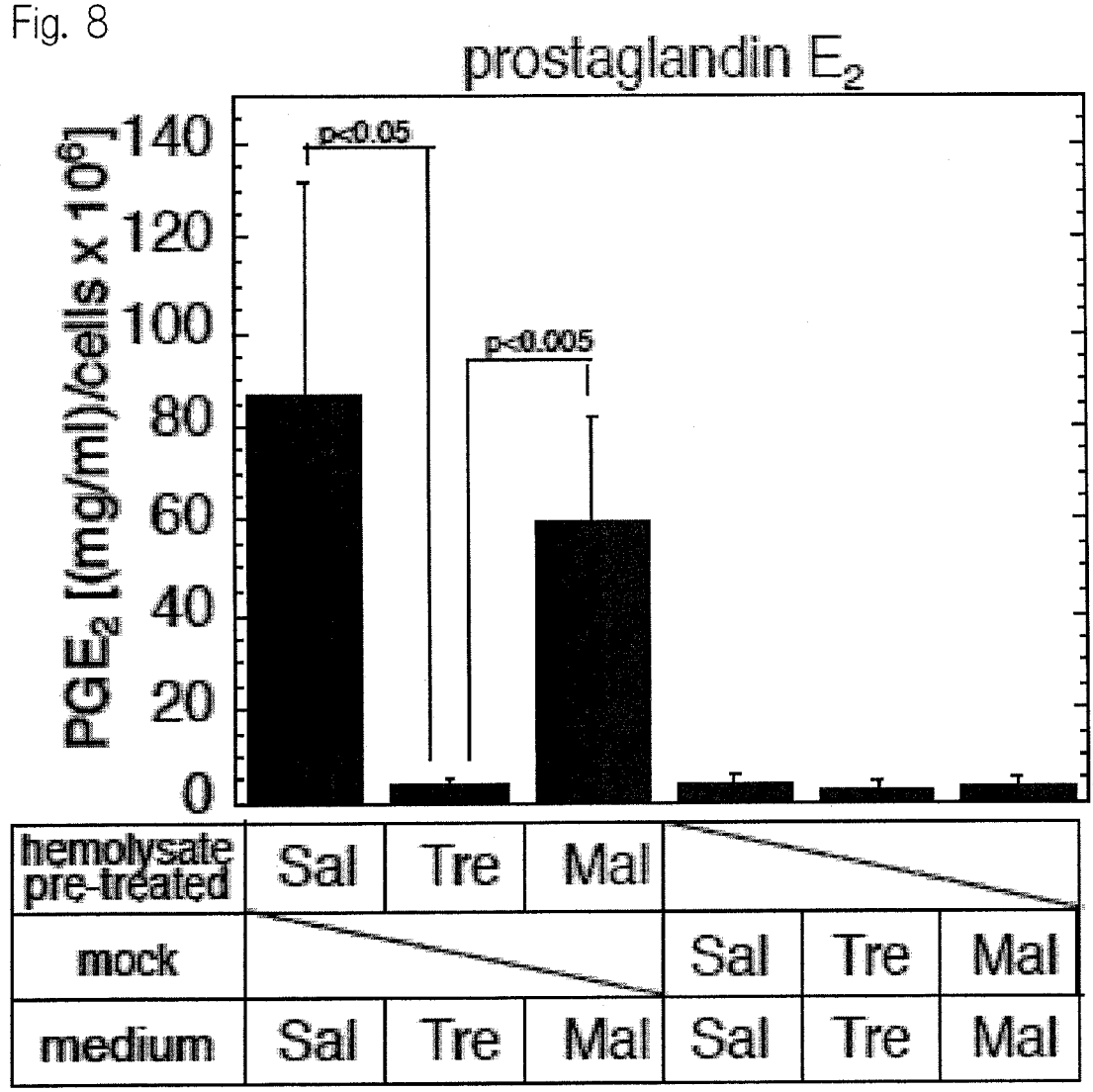
FIG. 8 is a graph showing trehalose's inflammation suppressing action ($PGE_2$ production-inhibiting action), as determined by using a vasospastic cell model, rat macrophage-like cells (RAW264.7).
Figure 9:
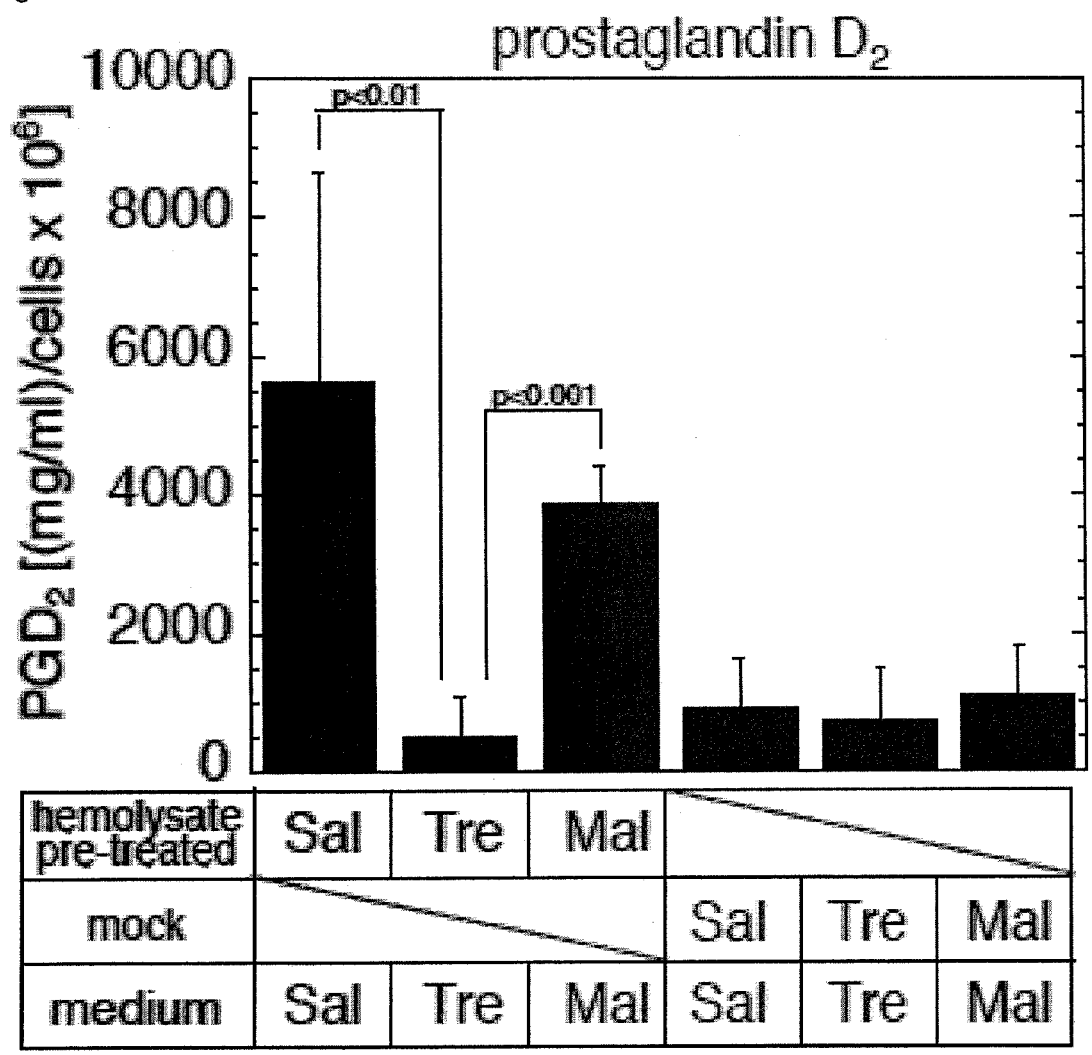
FIG. 9 is a graph showing trehalose's inflammation suppressing action ($PGD_2$ production-inhibiting action), as determined by using a vasospastic cell model, rat macrophage-like cells (RAW264.7).

Physiological saline (Sal), 10 wt % trehalose (Tre) and 10 wt % maltose (Mal) were added respectively to the blood collected from a rat (10 to 12 weeks of age, male) for pretreatment, and the mixture was processed in an ultrasonic homogenizer, to prepare an erythrocyte lysis solution. $1 \times 10^6$ or $2 \times 10^6$ of RAW264.7 cells were inoculated on a plate on the day before addition of the lysis solution, and were cultured in a medium comprising physiological saline, 5 wt % trehalose and 5 wt % maltose (respectively, as abbreviated to Sal, Tre and Mal) placed in an incubator (37° C., $CO_2$: 5%). The culture medium used was Dulbecco's Modified Eagle Medium (D-MEM) comprising 10% fetal bovine serum (FBS), penicillin and streptomycin. The next day, the lysis solution was added in an amount of 1/10 of the medium, and the mixture was incubated in the incubator (37° C., $CO_2$: 5%) for 18 hours. Then, the cells were washed with PBS; new medium was added; and the mixture was placed in the incubator (37° C., $CO_2$: 5%). The medium was collected after one hour for ELISA analysis. The ELISA was carried out by using Prostaglandin $E_2$ EIA kit-monoclonal (manufactured by Cayman) or Prostaglandin $D_2$ EIA kit (manufactured by Cayman). By the ELISA method, inflammatory reaction was induced by treating RAW264.7 with each lysis solution, and the influence of presence or absence of trehalose on production of $PGE_2$ (prostaglandin $E_2$) or $PGD_2$ (prostaglandin $D_2$), one of the final products in the arachidonic acid cascade, which plays the central role in inflammatory reaction, was studied (FIG. 8, FIG. 9: left column 3). For control, a lysis solution-untreated group (added respectively with physiological saline, trehalose and maltose) was also analyzed similarly (FIG. 8, FIG. 9: right column 3). Three or more independent tests were carried out to obtain the average, and the standard deviation obtained was expressed with error bars. The results are shown in FIGS. 8 and 9.

Study Result

FIG. 8 is a graph showing the anti-inflammatory action ($PGE_2$ production-inhibiting action) of trehalose, as determined by using a vasospastic cell model, rat macrophage-like cells (RAW264.7). FIG. 9 is a graph showing the anti-inflammatory action ($PGD_2$ production-inhibiting action) of trehalose, as determined by using a vasospastic cell model, rat macrophage-like cells (RAW264.7). The ordinate in the graph shown in FIG. 8 shows the $PGE_2$ concentration value (mg/ml) in cells ($1 \times 10^6$ cells). The ordinate in the graph of FIG. 9 shows $PGD_2$ concentration value (mg/ml) in cells ($1 \times 10^6$ cells). Thus, larger ordinate value means that a greater amount of $PGE_2$ or $PGD_2$ was produced. Mock indicates that the cells were treated with each solution comprising no lysis solution, and the cells treated with each solution comprising no lysis solution are a control group to the cells treated with each solution comprising the lysis solution. FIGS. 8 and 9 show that the amounts of production of $PGE_2$ and $PGD_2$ are significantly greater in the physiological saline (Sal) group than in the control group, and that the inflammatory reaction is induced by the lysis solution (FIGS. 8 and 9: compare Sal in left and right columns). The inflammatory reaction was also induced in the group comprising maltose (Mal), similarly to the physiological saline (Sal) group (FIGS. 8 and 9: compare Mal in left and right columns). Maltose, which is a molecule consisting of two glucose molecules similarly to trehalose (having exactly the same molecular weight and chemical composition), has a α1-4 bond, differently from trehalose, and is considered not to exhibit such a biological molecule-protecting function as trehalose has. On the other hand, the amounts of $PGE_2$ and $PGD_2$ were not increased under the condition where trehalose (Tre) was used, when compared with those in the control group, indicating that activation of the inflammatory reaction is suppressed almost completely (FIGS. 8 and 9: compare Tre in left and right columns). It was thus demonstrated that trehalose has an action to suppress the inflammatory reaction very efficiently that could be caused by the lysis solution.

EXAMPLE 3

Study (2) on the Inflammatory Action of Trehalose by Using Vasospastic Cell Model A vasospastic cell model was constructed by using normal human umbilical vein endothelial cells (HUVEC), for study on whether trehalose has anti-inflammatory action.

Method of Constructing Vasospastic Cell Model

Figure 10:
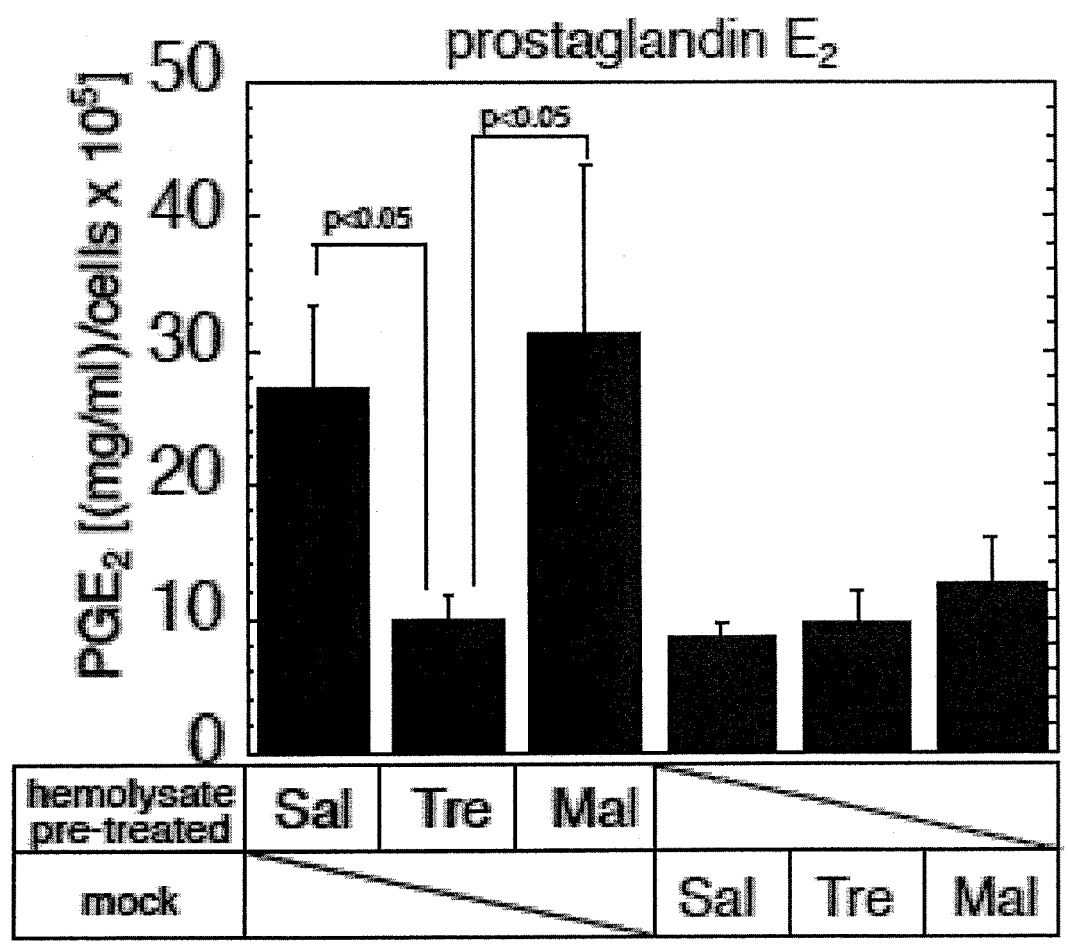
FIG. 10 is a graph showing trehalose's inflammation suppressing action ($PGE_2$ production-inhibiting action), as determined by using normal human umbilical vein endothelial cells (HUVEC).

Physiological saline (Sal), 10 wt % trehalose (tre) and 10 wt % maltose (Mal) were added respectively to the bloods collected from a rat (10 to 12 weeks of age, male) for pretreatment, and the mixture was processed in an ultrasonic homogenizer, to prepare an erythrocyte lysis solution. The HUVEC cells were inoculated on a plate in an amount of $1 \times 10^5$ cells on the day before the addition of the lysis solution and were cultured in an incubator (37° C., $CO_2$: 5%). The culture medium used was endothelial cell basic medium (EBM-2) comprising 2% fetalbovine serum (FBS), hEGF (human epidermal growth factor), heparin, hydrocortisone, ascorbic acid, VEGF (vascular endothelial growth factor), R3-IGF-1 (recombinant insulin-like growth factor-1), gentamicin and amphotericin-B. The next day, the lysis solution in an amount of 1/10 of the medium was added to the HUVEC cells, and the mixture was incubated in an incubator (37° C., $CO_2$: 5%) for 6 hours. The medium was then collected for ELISA analysis. The ELISA was carried out by using Prostaglandin $E_2$ EIA kit-monoclonal (manufactured by Cayman). Studied by the ELISA method was whether the inflammatory reaction was induced and there was any change in production of $PGE_2$ through treatment of the HUVEC cells with each lysis solution (FIG. 10: left column 3). The lysis solution-untreated group (added respectively with physiological saline, trehalose and maltose) was also analyzed similarly as a control group (FIG. 10: right column 3). Three independent tests were carried out to obtain the average, and the standard deviation obtained was expressed with error bars. The results are shown in FIG. 10.

FIG. 10 is a graph showing the anti-inflammatory action ($PGE_2$ production-inhibiting action) of trehalose, as determined by using normal human umbilical vein endothelial cells (HUVEC). The ordinate in FIG. 10 shows concentration value of $PGE_2$ (mg/ml) in cells ($1 \times 10^5$ cells). Thus, larger ordinate value means that a greater amount of $PGE_2$ was produced. Mock indicates that the cells were treated with each solution comprising no lysis solution, and the cells treated with each solution were a control group to the cells treated with each solution comprising the lysis solution. FIG. 10 shows that treatment with the lysis solution leads to increased production of $PGE_2$ also in HUVEC cells similarly to RAW264.7 cells, indicating that the inflammatory reaction was induced (FIG. 10: compare Sal in left and right columns). It also shows that, when the lysis solution pretreated with trehalose (Tre) was used, the induction of inflammatory reaction was suppressed (FIG. 10: compare Tre in left and right columns). The inflammatory reaction was induced when maltose (Mal) was used, similarly to the case where physiological saline (Sal) was used (FIG. 10: compare Mal in left and right columns).

The results above (FIGS. 8 to 10) demonstrate that trehalose has an action to suppress the inflammatory reaction induced by lysis solution at the molecule level in two different cells.

EXAMPLE 4

Study on the Vasospasm-Inhibiting Action of Trehalose by Using Rabbit Subarachnoid Hemorrhage Model Intracerebral blood flow was evaluated via perfusion-MRI method by using a rabbit subarachnoid hemorrhage model for analysis of the vasospasm-inhibiting action of trehalose.

Method of Constructing Rabbit Subarachnoid Hemorrhage Model

After magnetic resonance imaging (MRI) of a NZW rabbit (14 weeks of age, approximately 3.0 kg, male) in the normal state, the occipital region was shaved and the cisterna magna was punctured, and blood samples [group I: self blood+physiological saline (blood+Sal), group II: self blood+15 wt % trehalose solution (blood+Tre) and group III: physiological saline (Sal)] were injected into different test animals respectively in an amount of 3 ml. Additionally, 2 ml of blood sample and physiological saline (total of 5 ml) were injected to the same test animals by a similar method, two days later. Two days after the second administration, the influence of trehalose on cerebral vasospasm was evaluated via perfusion-MRI method (cerebrovascular normality is calculated by injecting a contrast medium through otic vein into the brain and determining the degree of recovery in brightness quantitatively) by using a high-definition MRI apparatus for animals (4.7 tesla, resolution: 50 μm) manufactured by Varian. Three independent tests were carried out to obtain the average, and the standard deviation obtained was expressed with error bars. The results are shown in FIG. 11.

Figure 11:
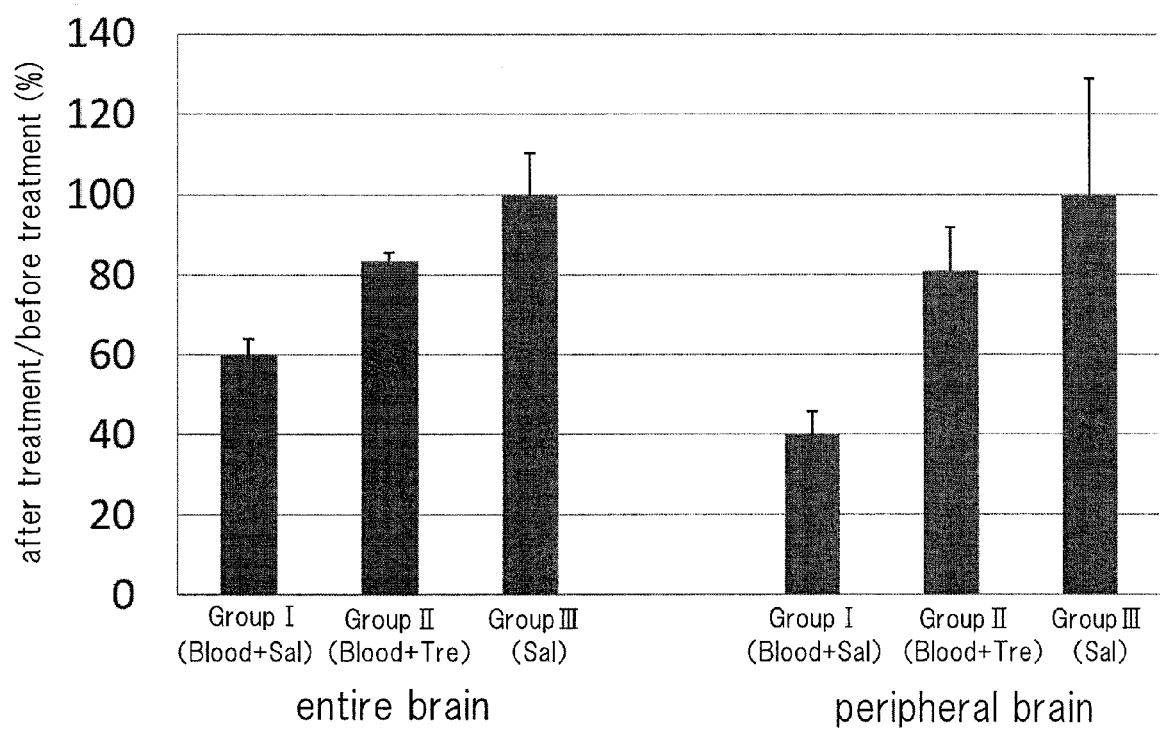
FIG. 11 is a graph showing trehalose's vasospasm-inhibiting action as determined by using a rabbit subarachnoid hemorrhage model and evaluating the intracerebral blood flow by perfusion-MRI method.

FIG. 11 is a graph showing the vasospasm-inhibiting action of trehalose, as determined by evaluating the intracerebral blood flow via perfusion-MRI method by using a rabbit subarachnoid hemorrhage model. The ordinate in FIG. 11 shows the percentage (%) of a value: [brightness after treatment/brightness before treatment]. Thus, larger ordinate value means that cerebrovascular normality is higher (vasospasm is more inhibited). The groups I to III in the left column of FIG. 11 show the evaluation results of entire brain. The groups I to III in the right column of FIG. 11 shows the evaluation results of peripheral brain. FIG. 11 demonstrates that, in the perfusion-MRI test, normality of cerebral blood vessel was higher in group I (group exposed to self blood+physiological saline), group II (group exposed to self blood+15 wt % trehalose solution), and group III (group exposed to physiological saline) in that order. The tendency was the same both in entire brain and in peripheral brain region. Assuming the normality of the physiological saline group (group III) was 100%, the normality of group I was approximately 60% and that of group II, approximately 80%. In addition, there was significant difference between groups I and II in t-test (paired t-test, one-sided test, p<0.01). The fact suggested that trehalose added during self blood administration suppressed intracerebral vasospasm.

EXAMPLE 5

Histological Analysis of Cerebral Vasospasm in Rabbit Subarachnoid Hemorrhage Model The vasospasm-inhibiting action of trehalose was analyzed via a histological method by using a rabbit subarachnoid hemorrhage model.

Method of Histologically Analyzing Cerebral Vasospasm

After the occipital region of a NZW rabbit (14 weeks of age, approximately 3.0 kg, male) was shaved and the cisterna magna was punctured, blood samples [group I: self blood+physiological saline (blood+Sal), group II: self blood+15 wt % trehalose solution (blood+Tre) and group III: physiological saline (Sal)] were injected into different test animals respectively in an amount of 3 ml. Additionally, 2 ml of blood sample and physiological saline (total of 5 ml) were injected to the same test animal by a similar method, two days later. Two days after the second administration, the animals were perfused with 4% paraformaldehyde for stabilization, and the brain stem and the basilar arteries were collected. The tissue was embedded in paraffin, cut into a section of 5 μm in thickness, and observed after hematoxylin-eosin staining (HE staining) The results are shown in FIG. 12.

Figure 12:
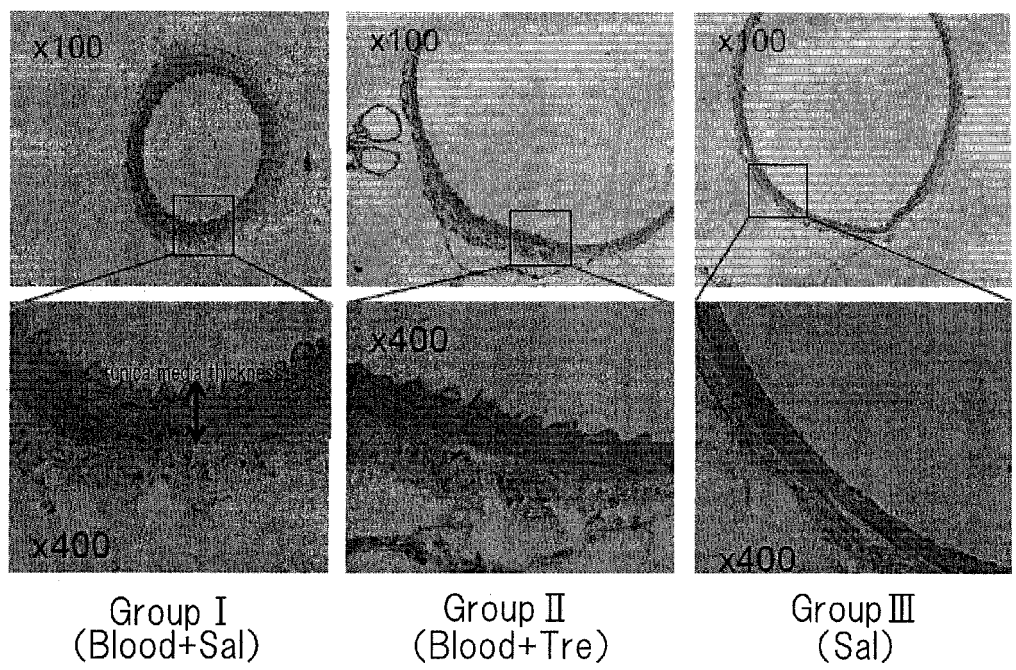
FIG. 12 is a photograph replacing a drawing, showing a tissue image of the basilar artery in a rabbit subarachnoid hemorrhage model.

FIG. 12 is a photograph replacing a drawing, showing a tissue image of the basilar artery in a rabbit subarachnoid hemorrhage model. FIG. 12 shows that the blood vessel diameter was reduced and the tunica media thickness was increased in group I (group exposed to self blood+physiological saline), in contrast to group III (group exposed to physiological saline) wherein no vasospasm was induced, indicating progress of vasospasm. On the other hand, in group II (group exposed to self blood+15 wt % trehalose solution), though some increase in tunica media thickness was observed, no reduction of the blood vessel diameter etc. were observed, and it is confirmed that vasospasm was suppressed definitely with respect to group I.

The above results show that trehalose is effective in inhibiting the vasospasm caused by exposure to blood vessel.

Figure 13:
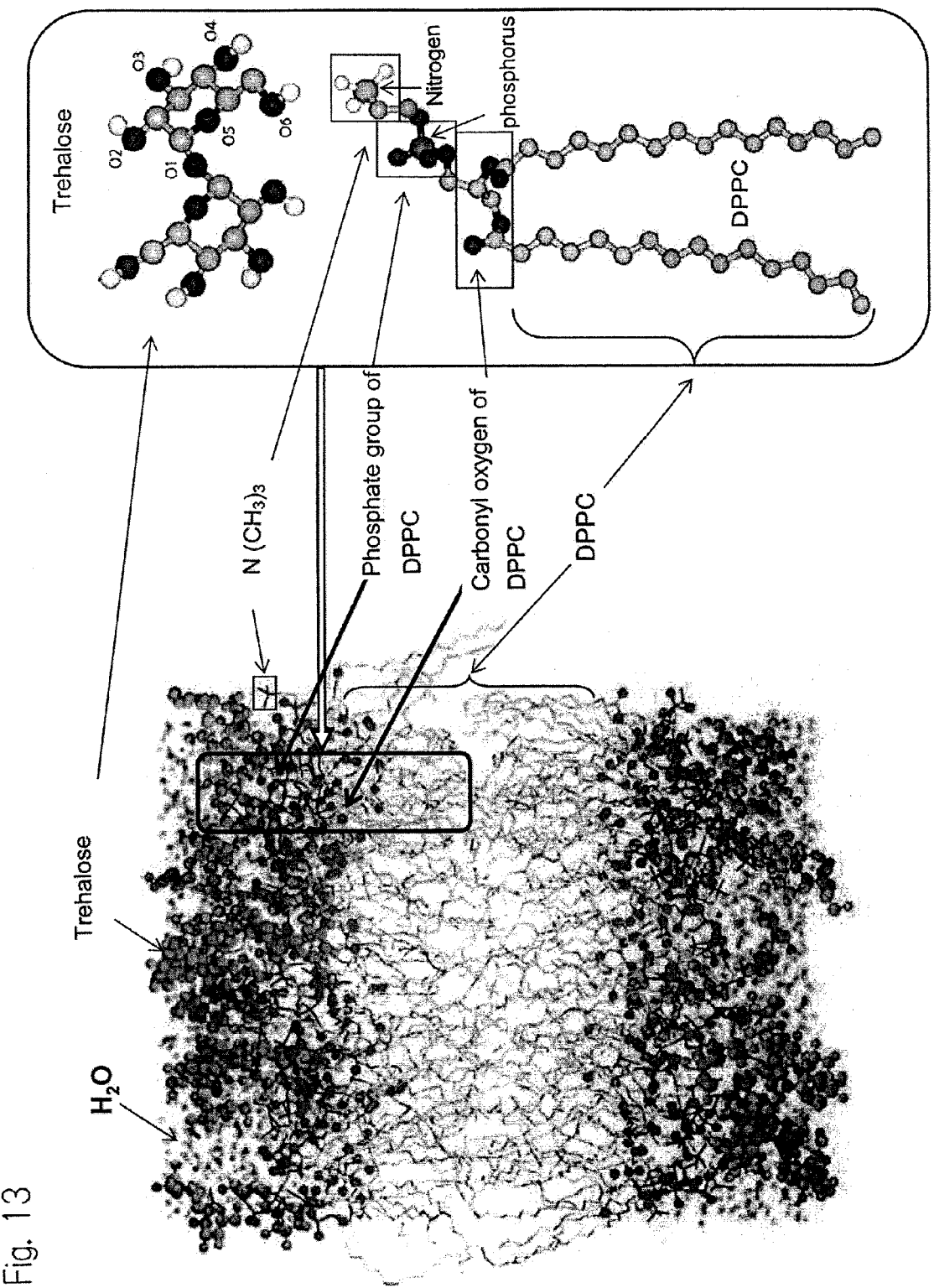
FIG. 13 is a chart showing a binding model of between trehalose and lipid membrane.

FIG. 13 is a chart showing a binding model between trehalose and dipalmitoyl phosphatidylcholine (DPPC) in lipid membrane. Trehalose is considered to bind to the lipid double membrane via carbonyl and phosphate groups by hydrogen bonding (modified from Biophys. J. 2005, 89: 4111-4121). It is considered that vasospasm is inhibited by binding of trehalose to cell membrane of lipid double membrane as described above.

Industrial Applicability

The present invention can be used in the field of medicine industry.

The invention claimed is:

1. A method of treating vasospasm, which comprises a step of administering to a host in need thereof an effective dosage of trehalose.

2. The method of claim 1, wherein said effective dosage of trehalose is from 0.1 mg to 40 mg per kg of body of said host.

3. The method of claim 1, wherein said vasospasm is a symptom in a disease selected from the group consisting of cerebral vasospasm, arterial vasospasm, vasospasm associated with transvascular operation, vasospasm associated with microsurgery of blood vessel, and vasospasm associated with placement of a stent or an embolization coil.

4. The method of claim 1, further comprising treatment of cerebral ischemia, cerebral infarction, and heart disease that are induced by vasospasm; inflammatory reactions associated with transvascular operation; and inflammatory reactions after placement of a stent or an embolization coil.

* * * * *